(12) United States Patent
Cardoso

(10) Patent No.: US 6,669,712 B1
(45) Date of Patent: Dec. 30, 2003

(54) NASAL OXYGEN CANNULA WITH SUPPLY TUBE MANAGEMENT

(76) Inventor: Norman Cardoso, 111 Ross Rd., Satsuma, FL (US) 32189

( * ) Notice: Subject to any disclaimer, the term of this patent is extended or adjusted under 35 U.S.C. 154(b) by 228 days.

(21) Appl. No.: 09/994,571

(22) Filed: Nov. 27, 2001

Related U.S. Application Data

(60) Provisional application No. 60/215,279, filed on Jun. 30, 2000.

(51) Int. Cl.[7] .............................................. A61M 29/00
(52) U.S. Cl. ............................... 606/199; 128/DIG. 26; 128/207.18; 128/200.24; 606/204.45
(58) Field of Search ........................ 128/200.24, 204.18, 128/207.14–207.17, 216.27, DIG. 26; 606/199, 204.45

(56) References Cited

U.S. PATENT DOCUMENTS

| | | |
|---|---|---|
| 2,245,969 A | 6/1941 | Francisco et al. |
| 2,590,006 A | 3/1952 | Gordon |
| 3,046,989 A | 7/1962 | Hill |
| 3,682,171 A | 8/1972 | Dali et al. |
| 3,871,373 A | 3/1975 | Jackson |
| 4,454,880 A | 6/1984 | Muto et al. |
| 4,660,555 A | 4/1987 | Payton |
| 4,808,160 A | 2/1989 | Timmons et al. |
| 4,932,943 A | 6/1990 | Nowak |
| 5,113,857 A | 5/1992 | Dickerman et al. |
| 5,172,688 A | 12/1992 | Dillon |
| 5,335,656 A | 8/1994 | Bowe et al. |
| 5,513,634 A | 5/1996 | Jackson |
| 5,513,635 A | 5/1996 | Bedi |
| 5,669,377 A * | 9/1997 | Fenn ..................... 128/200.24 |
| 5,685,292 A | 11/1997 | Fenn |
| 5,735,272 A | 4/1998 | Dillon et al. |
| 5,752,511 A | 5/1998 | Simmons et al. |
| 5,803,066 A | 9/1998 | Rapoport et al. |
| 5,817,039 A * | 10/1998 | Raunig ........................... 602/5 |
| 5,931,854 A * | 8/1999 | Dillon .................... 606/204.45 |
| 5,961,537 A * | 10/1999 | Gould .................... 606/204.45 |
| 5,976,173 A * | 11/1999 | Berke .................... 606/204.45 |
| 6,093,169 A | 7/2000 | Cardoso |
| 2003/0034030 A1 * | 2/2003 | Carlucci et al. ........ 128/200.24 |

FOREIGN PATENT DOCUMENTS

DE 229378 1/1910

* cited by examiner

Primary Examiner—Glenn K. Dawson
(74) Attorney, Agent, or Firm—Richard S. Vermut; Rogers Towers, P.A.

(57) ABSTRACT

A nasal cannula support device includes a generally L-shaped strut having a long leg and a short leg. The long leg of the device generally conforms to the ridge pole of the nose and is in an angular relationship with the short leg, allowing the short leg to pass around and under the tip of a user's nose. In one embodiment, the short leg includes a curved portion that secures and positions the nasal delivery stubs of an oxygen delivery barrel within a user's nostrils. In other embodiments, a cup-like area of the strut, between the long and short leg, provides finger-like projections that provide similar retention and positioning of the delivery barrel and stubs. The strut may be secured to the user's nose by an adhesive backing, tape, or forming the device to conform, closely, to the user's external nasal contour. The cannula support device also includes delivery tube management means so as to eliminate the need for uncomfortable ear loops and further stabilize the nasal cannula within the user's nostrils. A nasal breathing assistance device has a generally L-shaped strut having a long leg and a short leg and structure for securing the device to a user's nose. The nasal breathing assistance device leg is securable to a ridge pole of a user's nose in such a manner as to raise and shorten the tip of the user's nose resulting in an increase in diameter and decrease in length of the external nasal airway thereby facilitating inspiratory and expiratory air flow.

50 Claims, 4 Drawing Sheets

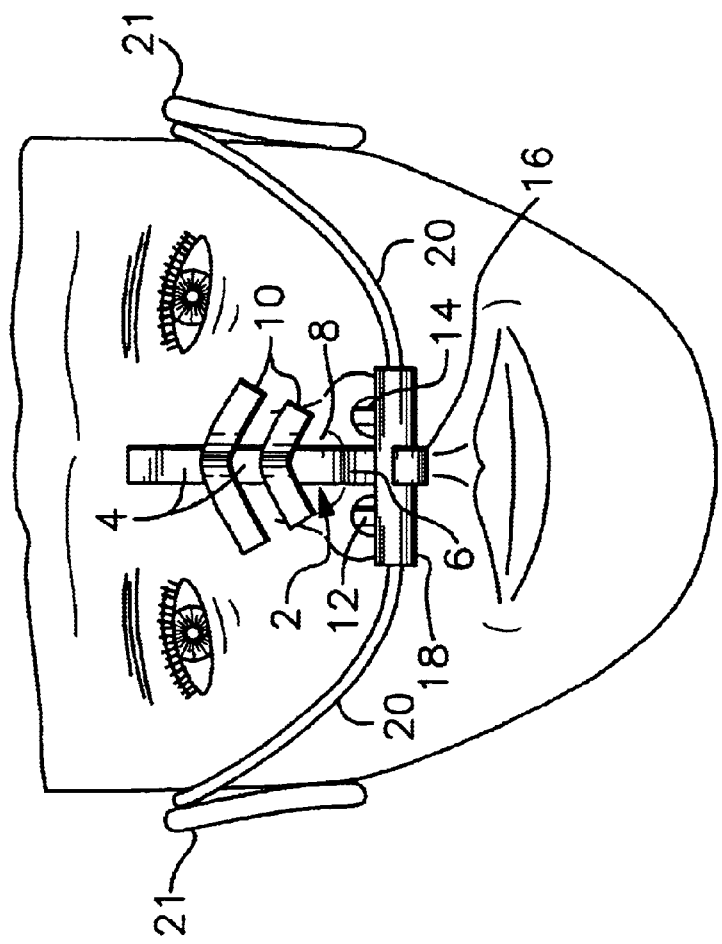
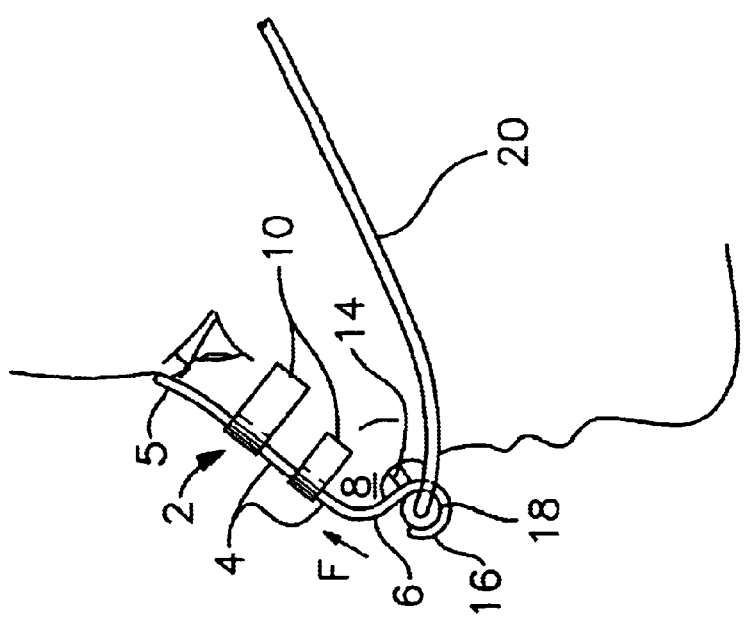
Fig. 1
Fig. 2

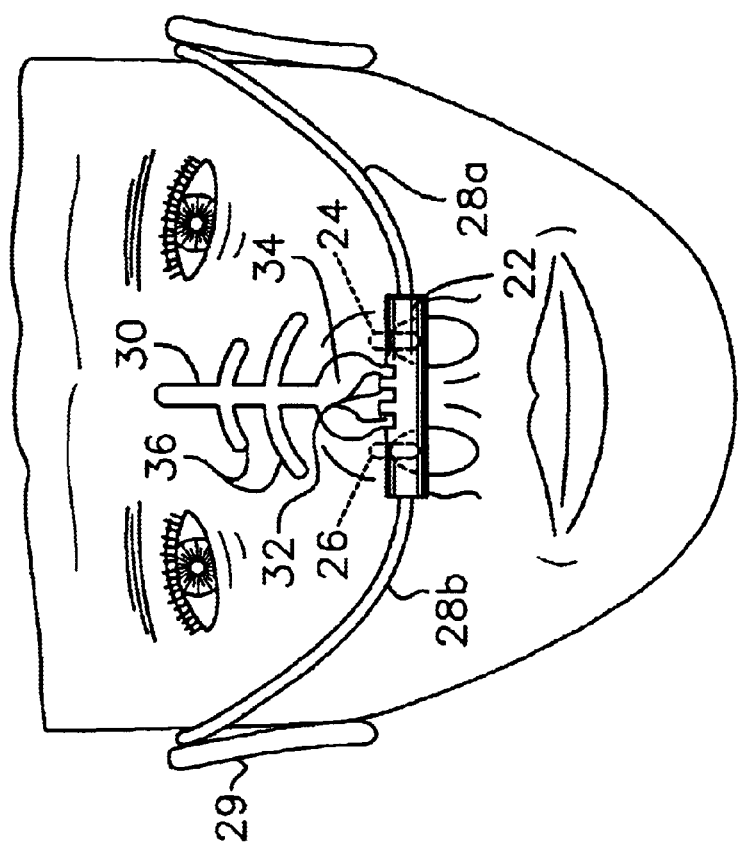
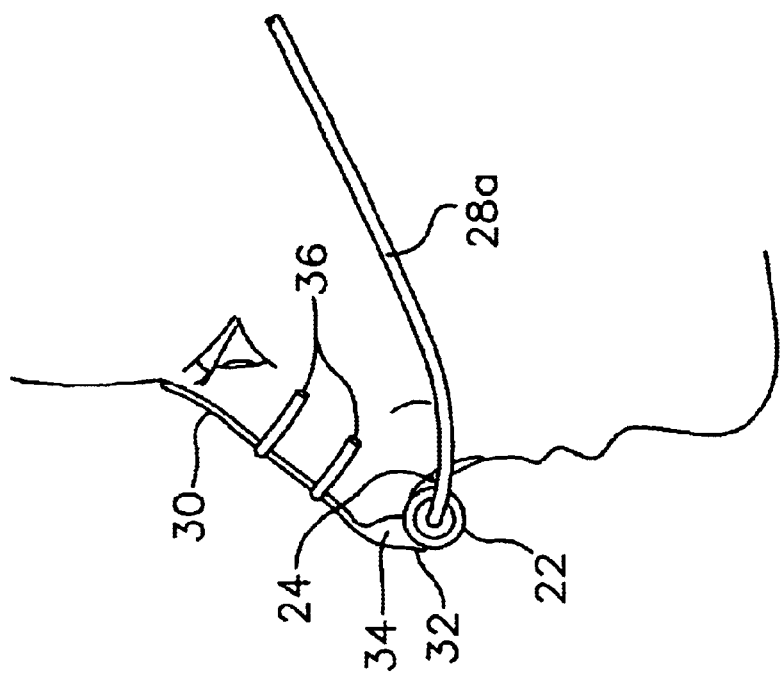
Fig. 4
Fig. 3

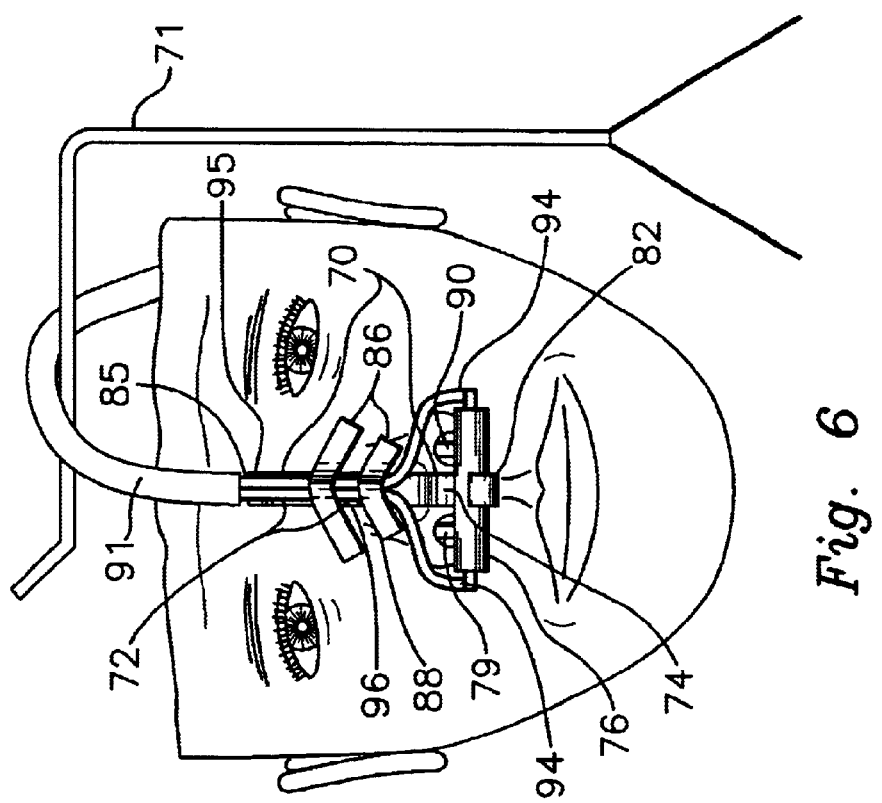
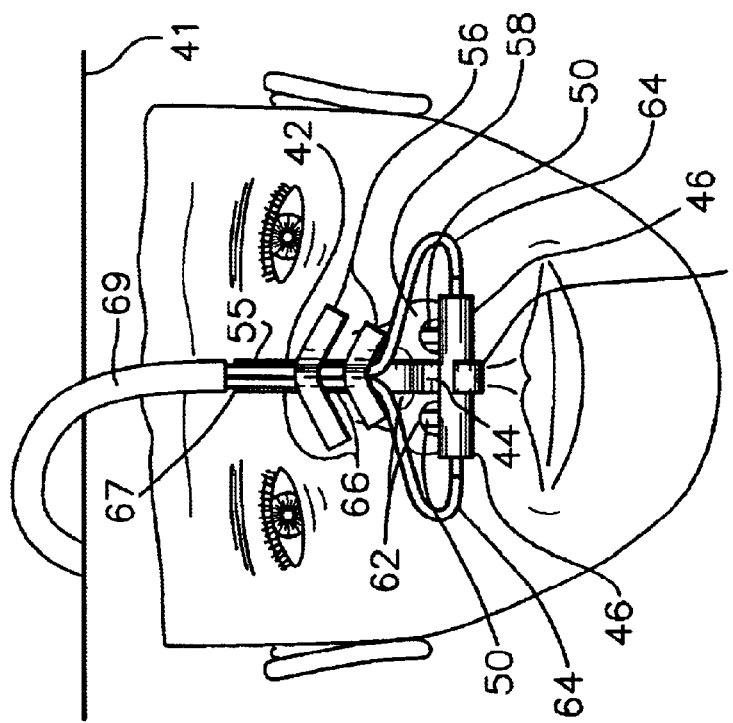
Fig. 6
Fig. 5

NASAL OXYGEN CANNULA WITH SUPPLY TUBE MANAGEMENT

This application claims the benefit of U.S. Provisional Application Ser. No. 60/215,279 file Jun. 30, 2000.

TECHNICAL FIELD

The present invention relates to nasal oxygen cannula technology. More specifically, the present invention pertains to devices and methods especially configured and adapted to stabilize and increase the retention of nasal oxygen cannulas while increasing the comfort of wearing same.

BACKGROUND OF THE INVENTION

Nasal oxygen cannulas are utilized to deliver oxygen directly to nasal airways in order to infuse oxygen into the inspirational air flow of patients in need of such therapy. Typically, these systems utilize a relatively large bore plastic supply tube as a conduit for providing gas flow from a pressurized oxygen source to proximal ends of a pair of plastic oxygen delivery tubes—having relatively smaller bores—. The pair of oxygen delivery tubes are ordinarily equal in length. The distal portions of the delivery tubes, conventionally, enter into opposite ends of a short, expanded piece of plastic tubing, referred to as an oxygen delivery barrel. Thus the oxygen delivery barrel acts to join and form a loop between the two oxygen supply tubes thereby providing a junction. The barrel is typically cylindrical in shape, formed of a short length of enlarged plastic tubing provided with small diameter, stub like extensions known as oxygen delivery stubs. The stubs are open at their distal ends and are positioned in circumferential alignment upon the barrel and at right angles,—or transverse—to the longitudinal axis of the barrel. The oxygen delivery stubs are positioned so that the distance there between approximates an average distance between the nostrils in which they will be positioned.

The bores of the oxygen supply tube, oxygen delivery tubes, oxygen supply barrel and delivery stubs are in fluid communication. Therefore, oxygen flowing from a pressurized oxygen source to the proximal end of the supply tube will flow through the supply tube and then on to the delivery tubes which will conduct the oxygen to the delivery barrel. As pressurized oxygen fills the barrel, oxygen will flow out from the stubs and into the nostrils of an individual in which the stubs are positioned. Thereafter, the patients own inspirational air flow will assist entry of the oxygen supplied by the catheter/cannula through the respiratory tract and into the lungs.

In order to properly provide oxygen delivery to a patient, oxygen catheter/cannulas must be maintained in a position wherein the delivery stubs are aligned with and retained within each of a patients nostrils. Conventional catheter/cannulas have largely depended upon the use of the pair of oxygen delivery tubes, connected to each end of the barrel, to stabilize the barrels position under the nose and thereby assist in maintaining the position of the oxygen delivery stubs within the patient's nostrils. By looping each of two delivery tubes over the top of each ear, a portion of the tube becomes trapped in the skin folds between the ear and the skin of the head medial thereto. The tension provided by trapping the tubes under the ear, prevents free movement of the delivery tubes and thus provides stabilization of the oxygen delivery barrel under and delivery stubs under a user's nose and within a user's nostrils.

Proximal to the ear folds—relative to the oxygen supply—the pair of delivery tubes junction with the larger diameter supply tube under the patients head. Alternatively, the delivery tubes may pass behind the ears, around the neck and under the patients chin where the tubes junction with the single supply tube.

The above-described method and apparatus does provide, in some circumstances, for limited oxygen cannula stabilization. In fact, utilizing the above-described conventional oxygen cannula without an ear loop will ordinarily result in rapid displacement of the delivery stubs upon movement of the patient's head. However, there are also many disadvantages and limitations related to utilizing this conventional apparatus and method. For example, patients do tend to move their heads during sleep. Therefore, there is an associated movement of the pair of oxygen delivery tubes looped behind the ears. Movement of these tubes often causes irritation, abrasion and pain arising from friction at the skin folds between the ear and head. As a result of such pain, patients often "shake off" the catheter/cannula in during the restless and interrupted sleep caused thereby. The frequent loss of the oxygen delivery stubs from the patients nostrils caused by shake off and displacement deprives the patient of required consistent oxygen therapy. In light of the current nursing shortage, the constant checking and supervision required by such an unreliable and high maintenance stabilization means is highly undesirable and, more importantly, ineffective. In addition, the afore-mentioned abrasion and irritation tend to interfere with patient rest as well as increasing the possibility that the catheter/cannula will be removed before adequate oxygen therapy is provided. The terms "nasal catheter/cannula", "nasal cannula", "nasal oxygen catheter/cannula" and "nasal oxygen cannula" as utilized throughout this specification and within the claims are interchangeable and refer, collectively and individually to a device comprised of an oxygen supply delivery, oxygen delivery tube, an oxygen supply barrel and nasal stubs utilized to provide oxygen delivery and/or enrichment therapy to a user by delivering oxygen directly to a user's external nasal airways.

U.S. Pat. No. 6,093,169 (the "169 patent") addresses, to some extent, the above-described catheter/cannula positioning/retention problems. In order to improve retention of the nasal oxygen delivery stubs within the nostrils, the '169 patent discloses the use of a detachable retainer which is positioned along the ridge pole of the nose. The ridge pole retainer, defining what may be described as an "L" shaped strut, has a long "leg" and a short "leg". The long leg of the strut is configured and adapted to generally conform to and lie upon the ridge pole of the nose from the root of the nose to an area proximate to the tip of the nose. The strut is comprised of a flexible material such as a plastic or fabric covered/padded metal framework. They may be secured to the ridge pole of the nose with a suitable adhesive means such as, for example, external tape or a self-adhesive backing. The short leg of the strut lies in an angular relationship with the long strut so that it may be positioned under the nose, generally in line with the nasal septum. In certain embodiments, a cup-shaped portion of the retainer, extending lateral to a junction of the long and short leg of the strut, is especially configured and adapted to capture the tip of the nose.

The short leg also includes, in certain preferred embodiments, a curved portion that is especially adapted and configured to pass around and securely hold an oxygen delivery barrel. The barrel is thus held and secured in a position and orientation that assures that delivery stubs arising therefrom remain well within a patients nostrils.

As described above, the device disclosed by the '169 patent is advantageously comprised of a springy plastic or springy metal backbone demonstrating high elastic memory within operational limits. The backbone is advantageously covered with a soft fabric padding. The elastic memory of the device, in combination with the contour and elastic nature thereof, provides a traction force to the nose when the device is secured along the ridge pole of a patient's nose. The device may be so secured by any suitable means including, for example, elastic strips or a self-adhesive backing. The traction force of the device, so applied and secured, tends to pull the tip of the wearer's nose both upward and inward. More specifically, as the long arm of the retainer, contoured to approximate to the ridge pole is urged upward towards the root of the nose (due to its shape, spring tension and the effect of the adhesive strips and/or backing), the cup-shaped portion pulls the tip of the nose upward and inward towards the forehead. The pulling upward and inward of the tip of the nose, in turn, tends to shorten and increase the diameter of the external nasal airway as compared to bore status without the device. As a result, the external nasal bore, widened and shortened, provides decreased airway resistance—allows greater inspiration— and thus more efficient oxygen delivery—. At the same time, the device provides great stabilization and retention to the oxygen delivery barrel and delivery stubs under the nose and within the nostrils.

Although the device described by the '169 patent provides increased catheter/cannula stabilization, it is still utilized with the above-described ear loops in order to further stabilize the device. Thus, although greater stability is provided by the cannula support device described therein, a patient is still at risk for the irritation, abrasion and resultant "throw off" associated with such loops.

What is needed is a catheter/cannula device and method of utilizing same, which provides the increased stabilization and increased airway efficiency demonstrated by the '169 patent, while, at the same time, eliminating the use of ear loops and the irritations and abrasions associated with the use thereof.

SUMMARY OF THE INVENTION

Now in accordance with the present invention, a nasal catheter/cannula support device is disclosed providing improved nasal catheter/cannula positioning while, at the same time, eliminating the need to utilize ear loops for the retention and stabilization thereof. In a first preferred embodiment of the present invention, a nasal catheter/ cannula support device utilizes a ridge pole retainer to stabilize a nasal catheter/cannula. The ridge pole retainer of the present invention is comprised of a generally "L"-shaped strut having a long leg and a short leg. The long and short legs of the strut are in such an angular relation so as to allow the short leg to pass around and under the tip of the user's nose when the long leg is aligned with the ridge pole region of the nose. Each of the embodiments of the present invention include an oxygen delivery tube management means associated with the long leg of the strut for positioning and retaining the delivery tube(s).

The long leg of the strut is advantageously shaped and configured so as to approximate nasal ridge pole contour. The strut is advantageously formed of a material with sufficient elastometric and elastic memory properties so as to allow the strut to be easily biased into intimate contact a ridge pole region of a patient's nose, while at the same time, exerting force stored thereby, within the material urging the strut back to its original shape.

The short leg of the strut is continuous with and generally in an angular relationship with the long leg so as to generally pass around and under a patient's nose when the long leg is in general alignment with the nasal ridge pole. A distal—or inferior—portion of the short leg may advantageously include, in certain embodiments, a curved section especially configured and adapted for securing an oxygen delivery barrel in a functional position under a patients nose so that the nasal delivery stubs located on the barrel are held and maintained within a patient's nostrils. Alternatively, a curved cup-shaped portion of the ridge pole retainer, extending laterally from the junction of the short and long legs, may be utilized to capture the nasal tip. The cup-shaped portion extends laterally so as to encompass the tip of the nose and may advantageously includes a plurality of finger-like extensions especially configured and adapted for securing an oxygen delivery barrel to the retainer device. The finger-like extensions also act to align the oxygen delivery stubs of the oxygen delivery barrel within patient's nostrils—also preventing rotation and other displacement of the stubs and barrel—.

The nasal catheter/cannula support device of the present invention includes a means of securing catheter/cannula delivery tubes thereto. More specifically, the ridge pole retainer includes a means for securing oxygen delivery tubes to the long leg of the strut so as to obviate the need to use ear loop retention. In certain embodiments of the present invention, adhesive is utilized to affix the delivery tubing to the long leg. For example, adhesive tape or adhesive bonding material may be utilized. In other embodiments, the long leg of the ridge pole retainer is provided with a plurality of finger-like projections having little to no elastic memory. The finger-like projections of the long leg are selected to demonstrate a diameter and length sufficient to allow said projections to be bent around, engage and stabilize delivery tubing upon the long leg of the retainer. Alternatively, the delivery tube(s) may be molded to (or fused) to the long leg when the long leg is comprised of a plastic material Alternatively other means of joining the delivery tubes, such as, for example, fabric having hook and loop fastening extensions means and nylon ties may also be advantageously selected.

In utilizing the support structure of the present invention, an oxygen supply barrel is positioned within the curved portion of the short leg—or by means of the aforementioned finger-like projections of the cup-shaped portion of the strut—so that oxygen supply stubs located upon the barrel are positioned on either side of the long axis of the short leg and in a direction in general alignment with the long leg. The oxygen supply barrel is connected to and in fluid communication with a pair of oxygen delivery tubes which, in turn are connected to an oxygen supply tube and a pressurized oxygen source. The device is then positioned against a patient's nose so that the long leg is biased into intimate contact with the nasal ridge pole thereof. At the same time, the device is also positioned so that the short leg curves around and under the tip of the nose. In embodiments of the present invention utilizing a cup-shaped region, said region is held in intimate contact with the tip of the user's nose. The device is held in the afore-mentioned position by means, for example, such as adhesive tape placed along, and generally, perpendicular to the long leg. In other embodiments, the long leg may be provided with an adhesive backing. As the device, due to its elastic memory, attempts to regain an original, unbiased shape, the forces generated thereby tend to elevate and shorten the tip of the nose, in turn causing the external nasal airway to shorten and increase in bore. At the same time, the device, by means of the above-described curved portion of the short legs—and in certain embodiments, finger-like projections of the cup-shaped portion—retains the oxygen delivery barrel under the nose and the oxygen delivery stubs within the patient's nostrils. As discussed in further detail below, certain embodiments of the present invention provide struts so closely shaped and adapted to the external surface contour of a user's nose as to obviate the need for adhesive fixation of the strut to the nose.

In a first preferred embodiment of the present invention, the oxygen supply barrel is selected to be of a "conventional" type, with fluid connection thereto provided at opposite ends of the delivery barrel as has been known to the prior art. Therefore, in practicing the first preferred embodiment of the present invention, a pair of oxygen delivery tubes, in fluid communication with opposite ends of the barrel, are looped up to, and brought in parallel contact, along the midline of the longitudinal axis of the long leg of the retainer. The delivery tubes, thus approximated and positioned, are then held in place along the retainer a securing means. The securing means may be advantageously selected to be, for example, a bonding agent, cement or adhesive tape. The securing means may also be selected to be retentive fabric demonstrating hook and loop fastening such as Velcro(TM) or nylon tie devices. In addition, small, pliable metal extensions may be provided upon the long leg so as to allow fixation of the delivery tubes in axial alignment with the strut. The loop produced by directing the oxygen delivery lines from the opposite ends of the oxygen supply barrel upward so as to join at the long leg of the retainer is relatively small and extends a small distance, lateral to the user's nose, as compared to the ear loop of the prior art. The diminutive nature of the loop is of great importance as such small loops define relatively short lever arms. Thus, since the loops do not extend, substantially, laterally from the long axis of the nose and ridge pole retainer, movement of these loops results in diminutive displacement force transfer to and/or torsion of the catheter/cannula.

Above and beyond the ridge pole retainer, the delivery tubes are held together by means of adhesive. They may also be held together by any other suitable means such as, for example, fabric strips, adhesive tape, nylon ties, or elastic bands. It is also contemplated that the delivery tubes utilized in practicing the present invention may be formed together, from a point where the tubes meet and are held at the long leg of the retainer, until they junction with the oxygen supply tube. In all such embodiments, the tubing is directed over the patients forehead where it junctions with the supply tube above and behind the patient. Thus, the first preferred embodiment of the present invention, as all embodiments thereof, avoid the use of ear loops for catheter/cannula stabilization and retention.

In a second preferred embodiment of the present invention, the oxygen supply barrel is provided having oxygen delivery tube connections located at opposite ends thereof. However, unlike oxygen delivery barrels of the prior art, the oxygen barrel utilized in practicing the second preferred embodiment of the present invention provides delivery line entry into the barrel at right angles to the long axis thereof. The entry of the delivery tubes into the delivery barrel may be advantageously selected to be in substantial circumferential alignment with the nasal oxygen delivery stubs thereof so that the delivery tubes, as discussed below, may be guided towards the ridge pole and long leg of the retainer to which said tubes are affixed—with a minimum of curvature and/or turns required therefore. The delivery tubes, which are in fluid communication with the barrel, may be connected to the barrel via right angle fittings located at opposite ends or proximate opposite ends of the barrel. In the alternative, the barrel utilized in practicing the second preferred embodiment of the present invention may incorporate, as an integral feature, delivery tubes entering the barrel at the afore-mentioned right angle orientation which are fused and/or molded to the oxygen delivery barrel. Therefore, as the delivery tubes exit the oxygen supply barrel, a minimum of looping or lateral excursion of the tubes is necessary in order for the tubes to meet and be affixed along the midline of the long leg. Only a slight curvature towards the long axis of the retainer is required in order to align the tubing therewith. As in the case of the first embodiment, the tubing may be affixed to the long leg by any suitable means such as, for example, a bonding agent, cement or adhesive tape. The securing means may also be selected to be retentive fabric such as Velcro(TM) or nylon tie devices. In addition, small, pliable metal extensions may be provided upon the long leg so as to allow fixation of the delivery tubes in axial alignment with the strut. The second preferred embodiment avoids the required ear loop of the prior art as well as the diminutive loop produced in utilizing the device and practicing the method of the first preferred embodiment herein. The second preferred embodiment does require that delivery tubing run lateral to the midline of the ridge pole and retainer. However, the lever arm produced by such diminutive lateral placement allows little if any translation of head movement—and resultant movement of delivery lines, into torsional or other displacement forces that would otherwise act to dislodge or disturb catheter/cannula placement.

As in the case of the first preferred embodiment, above and beyond the ridge pole retainer, the delivery tubes are held together by a suitable means such as, for example, an adhesive. They may also be held together by any other suitable means such as, for example, fabric strips, adhesive tape, nylon ties or elastic bands. It is also contemplated that the delivery tubes utilized in practicing the present invention may be formed together, from a point where the tubes meet and are held at the long leg of the retainer, until they junction with the oxygen supply tube. In all such embodiments, the tubing is directed over the patients forehead where it junctions with the supply tube above and behind the patient. Thus, the second preferred embodiment of the present invention, like all embodiments thereof, avoid the use of ear loops for catheter/cannula stabilization and retention.

In the third preferred embodiment of the present invention, an oxygen supply barrel is provided having an oxygen delivery tube connection located approximately at the middle of the length thereof. The delivery line connection is oriented so as to be transverse to, and approximately midway between the ends of the oxygen delivery barrel. Therefore, the oxygen delivery tube is positioned on the barrel in such a manner that it may be affixed to the long leg of the retainer with only a minimum of curvature and substantially no lateral extension. The oxygen supply barrel of the third preferred embodiment may be provided with a tube fitting for receipt of the single oxygen delivery tube utilized thereby, or, in the alternative, the barrel may incorporate an integral delivery tube located at the afore-mentioned midline position with the oxygen delivery stubs being located lateral to, and on either side of the tube. Unlike oxygen delivery barrels of the prior art, the oxygen barrel utilized in practicing third preferred embodiment of the present invention provides a fitting or, in some examples, an integral delivery tube that allows a single delivery hose to enter the supply barrel. The delivery tube enters the oxygen delivery barrel at a point substantially aligned with the nasal septum separating the nostrils. The third preferred embodiment of the present invention therefore avoids lateral extension of delivery tubing beyond the midline of the nose and thus is highly resistant to the transfer of torsional or other displacement forces to the catheter/cannula.

As in the case of the first and second embodiment, the single midline delivery tube connected to the middle of the oxygen barrel may be affixed to the long leg by any suitable means such as, for example, a bonding agent, cement or adhesive tape. The securing means may also be selected to be retentive fabric, such as Velcro(TM), or nylon tie devices . In addition, small, pliable metal extensions may be provided upon the long leg so as to allow fixation of the delivery tubes in axial alignment with the strut. The third preferred embodiment of the present invention avoids the required ear loop of the prior art, the reduced and diminutive loop produced in utilizing the device and practicing the method of the first preferred embodiment, and the diminutive curvature associated with the second preferred embodiment herein.

As in the case of the first and second preferred embodiments above-described, above and beyond the ridge pole retainer, the delivery tubes are held together by a suitable means such as an adhesive. The may also be held together by any other suitable means such as, for example, fabric strips, adhesive tape, nylon ties or elastic bands. It is also contemplated that the delivery tubes utilized in practicing the third embodiment of the present invention may be formed together, from a point where the tubes meet and are held at the long leg of the retainer, until they junction with the oxygen supply tube. In all such embodiments, the tubing is directed over the patients forehead where it junctions with the supply tube above and behind the patient. Thus, the third preferred embodiment of the present invention, like all embodiments thereof, avoid the use of ear loops for catheter/cannula stabilization and retention.

In each of the above-described embodiments, the oxygen supply barrel may be provided as an integral part of the cannula/catheter support structure. In such cases, the barrel may be fused to the remainder of the structure, or held in place by a combination of fusion and the use of fixation "fingers" arising from the cup-shaped laterally extended portion and thereafter penetrating the selected barrel. In other embodiments, the barrel may be a separate and distinct component, held in position by the curved portion of the short leg as described above.

In each of the afore-mentioned embodiments of the present invention, unifying the cannula supply tubes over the long arm of the support strut reduces and or eliminates a lever arm produced by the relatively large loops formed lateral to the ends of the oxygen supply barrel by the cannula supply tubes. Avoiding and/or reducing the magnitude of these lateral loops greatly reduces the application of torsional forces—applied by the these lateral cannula supply loops and initiated by head movement—upon the barrel. Reduction of such torsion forces upon the barrel, in turn, reduces the frequency and degree of oxygen supply nub movement and displacement. In addition, stabilizing the cannula supply line(s) via fixation to the strut obviates the need for ear loop stabilization which, as discussed above, is causative of skin fold abrasions, irritations and "shaking off" of cannulas during sleep.

Therefore, the present invention provides an improved catheter/cannula stabilization device and method of utilizing same demonstrating increased cannula stabilization while, at the same time, eliminating a fundamental cause of cannula loss/displacement—ear loop irritations/abrasions—. Thus the present invention reduces the frequency of cannula loss/displacement, decreases the need for replacement of same by nursing staff, and increases patient comfort (and thus undisturbed sleep.) In view of the current nursing shortage, as well as the great expense of recruiting additional nursing staff, the reduction in need for cannula repositioning and replacement by staff, provided by the present invention, is of great economic benefit to both patients and health care facilities alike.

The first, second and third preferred embodiment of the present invention may advantageously and additionally incorporate the use of a straight edge surface, above and behind the patient's head, and parallel to the floor. This straight edge is provided at a point behind and above the patient's head. By running the delivery lines—which, in the case of paired tubes, are joined together, distal to the retainer by the means described above—over the patient's forehead and thence up and over a suitable straight edge, free movement of the tubing greatly relieves tension on the catheter/cannula during head and body movements. More specifically, the oxygen delivery tube(s), affixed along the long leg of the strut and joined to an single oxygen supply tube at or proximal to the strut, is passed directly back and across the patient's forehead. The supply line then passes over the straight edge parallel to the floor and slightly above the patient's head. The parallel edge allows smooth and rapid movement of the supply tube without causing any torsion or traction forces to be applied to the catheter/cannula during head movement. The straight edge utilized may be, for example, a hanger fitted to an IV stand or hospital bed. In some instances, the a headboard may provide a suitable surface. Alternatively, the tubing could pass through an elevated round loop. In certain embodiments it may be advantageous to apply a minor amount of weight, just sufficient enough to prevent tangling of the tubing on the distal side of the hole or straight edge. In this way, patient movements would not allow for the formation of tangles. However, the tension must be kept sufficiently low so as to avoid any restriction of patient head movement.

In a first alternate embodiment of the present invention, the catheter/cannula support device of the present invention can be utilized without a catheter/cannula or an oxygen source and still provide increased respiratory performance. In this embodiment, the shortening and increase in bore diameter of the external nasal passages increases breathing efficiency. This embodiment can be of great benefit to patients suffering from nasal congestion and or anatomic deformation which tend to obstruct the nasal passages. The increase in external nasal bore with a simultaneous decrease in passage length results in a significant decrease in resistance to gaseous exchange. Thus, the need for mouth breathing is reduced, respiration is facilitated and associated snoring may be eliminated. It is also believed that the reduction in breathing related stress may also reduce the risk of an untoward cardiac events.

BRIEF DESCRIPTION OF THE DRAWINGS

FIG. 1 is a side view of a ridge pole nasal oxygen catheter/cannula retainer utilizing ear loops.

FIG. 2 is a frontal view of a ridge pole nasal catheter/cannula retainer utilizing ear loops.

FIG. 3 is a side view of a ridge pole nasal catheter/cannula retainer utilizing ear loops.

FIG. 4 is a frontal view of a ridge pole nasal catheter/cannula retainer utilizing ear loops.

FIG. 5 is a frontal view of a ridge pole nasal catheter/cannula retainer of the first preferred embodiment utilizing a conventional in-line oxygen barrel oxygen delivery tube connection.

FIG. 6 is a frontal view of a ridge pole nasal catheter/cannula retainer of the second preferred embodiment utilizing right angle oxygen barrel tube junction.

DETAILED DESCRIPTION

Figure 7:
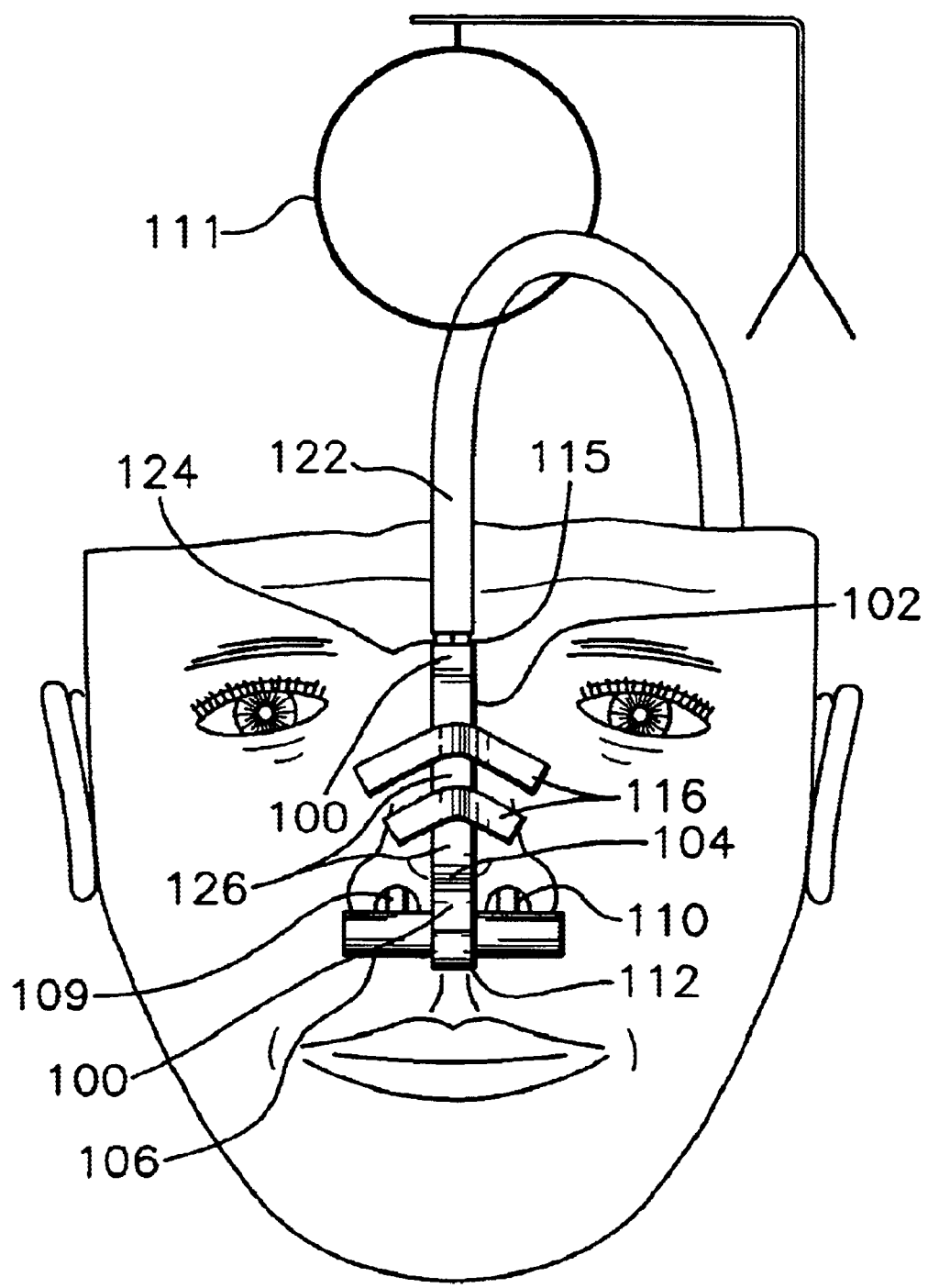
FIG. 7 is a frontal view of a ridge pole nasal catheter/cannula retainer of the third preferred embodiment utilizing an oxygen delivery barrel having a single, mid entry delivery line connection.

FIGS. 1, 2, 3 and 4 illustrate nasal oxygen catheter/cannula retaining devices of the prior art utilizing ear loop technology for providing increased catheter/cannula stabilization. The retainer is comprised of a generally "L"-shaped strut 6 having a long leg 4 and a short leg 6. The strut is secured to the nose 8 by means of tape 10, adhesive materials, adhesive backings or, in some instances, by conforming to the shape of the patient's nose so precisely as to remain in place without need of fixation means. The strut is extended superiorly to the root 5 of the nose. The short leg 6 of the strut 6 includes a curved portion 16 especially shaped, configured and adapted for receipt and retention of an oxygen delivery barrel 18. The oxygen delivery barrel 18 includes 2 oxygen delivery stubs 14 in fluid communication, proximally, with the oxygen delivery barrel 18 and distally, with a user's nostrils. The barrel 18 is also in fluid communication with the distal ends of the oxygen delivery tubes 20. An oxygen supply source provides pressurized oxygen to an oxygen supply tube which, in turn, communicates at a distal end thereof with proximal ends of the delivery tubes 20.

By placing the retainer upon a patient's nose 8, and urging the long leg of the strut against the ridge pole of the nose and upward towards the root 5, the resulting flexing of the strut, in restoring the original shape thereof, tends to move the tip of the nose upward and inward, thereby shortening and widening the external nasal passages as compared to the undisturbed nasal bore. The increased diameter and shortened length of the nasal passage increases air flow—including air flow necessary to sweep infused oxygen into the lungs—. At the same time, the device is highly effective in positioning the oxygen delivery stubs deep within the nostrils and providing substantial retention thereof.

FIG. 3 and 4 illustrate nasal a nasal oxygen catheter/cannula retaining device of the prior art utilizing ear loop technology for providing increased catheter/cannula stabilization and utilizing a cup-shaped region 34 located at the end of a nose strap 30. Three fingers 32 extending from the cup shaped region are utilized to secure oxygen delivery barrel 22. Oxygen delivery stubs 24 and 26, positioned on said barrel and in fluid communication therewith, are oriented and positioned by said fingers 32 so as to maintain said stubs 24 and 26 within a patient's nostrils 25. The nose strap 30 is provided with an adhesive backing, or can utilize tape 36 in order to affix the strap against the ridge pole of the nose and biased upwards, towards the root of the nose. Upon placement of the strap against the nose and upwards towards the root thereof, the cup-shaped portion of the retainer retracts the tip of the nose inwards while simultaneously lifting same. Thus the cup-shaped portion of this device serves the same functional purpose as the short leg of the device illustrated in FIGS. 1 and 2, above.

Each of the afore-mentioned catheter/cannula devices of the prior art utilize ear loop tube routing and catheter/cannula retention technology. In FIG. 2 and FIG. 4 oxygen delivery tubes 20 and 28a are looped about the ear 21 and 29. Movement of a patient's head during sleep, or at any other time, causes movement of the delivery tubing between the patient's ear and the skin thereunder referred to as skin folds. Skin fold irritation leads to shaking off of the device by a patient—mostly during restless sleep occasioned by the irritation and abrasion caused by such movement—. Also, the conventional tubing routing illustrated in the FIGS. 1–4 require lateral extension of tubing on either side of the catheter/cannula. Such large lateral extensions form substantial lever arms amplifying torsional and other displacement forces generated by head rotation and tube movement.

FIG. 5 illustrates a first preferred embodiment of the present invention obviating the need for ear loop technology. The retainer illustrated in FIG. 5, utilizes a curved portion 52 of short leg 44 in order to retain, stabilize and position oxygen barrel 46 under the nose and oxygen delivery stubs within the nostrils 50. The retainer is comprised of a generally "L"-shaped strut 40 having a long leg 42 and a short leg 44. The strut is secured to the nose 58 by means of tape 56, adhesive materials, adhesive backings or, in some instances, by conforming to the shape of the patient's nose so precisely as to remain in place without need of fixation means. The strut is extended superiorly to the root 55 of the nose. The short leg 44 of the strut 40 includes a curved portion 52 especially shaped, configured and adapted for receipt and retention of an oxygen delivery barrel 46. The oxygen delivery barrel 46 includes 2 oxygen delivery stubs 62 in fluid communication with the oxygen delivery barrel 46 and distal ends of the oxygen delivery tubes 64. However, it is equally contemplated that, in addition to the aforementioned short leg, a cup-shaped portion of the strut, generally at a similar angular relation with the long leg, may incorporate finger-like projections to retain, position and stabilize the oxygen delivery barrel and the oxygen delivery stubs arising therefrom.

An oxygen supply source provides pressurized oxygen to an oxygen supply tube 69 which, in turn, communicates at a distal end thereof with proximal ends of the delivery tubes 67. However, unlike the prior art, the oxygen delivery tubes arising from the ends of the supply barrel 46 are not routed to form ear loops. The delivery tubes 64 are instead looped upward towards the long leg 42 of the L-shaped strut 40 where the tubes are held in close proximity to each other as well as the midline of the long leg 42 by means of tube retention pins 66. However, adhesives, adhesive tape, cements, bonding agents, nylon ties and any other means capable of joining the supply lines to each other and the long leg may be utilized and are contemplated by the present invention. The distribution lines are joined together, above the long leg. This may be accomplished by molding the tubes to such a configuration, utilizing adhesives or any other fixation means. Thereafter, the delivery tubes are routed over the forehead and on to an oxygen supply tube.

By placing the retainer upon a patient's nose 68, and urging the long leg of the strut against the ridge pole of the nose and upward towards the root 55, the resulting flexing of the strut, in restoring the original shape thereof, and in opposition to means and forces securing the strut to the user, tends to move the tip of the nose upward and inward, thereby shortening and widening the external nasal passages as compared to the undisturbed nasal bore. Adhesive backing, adhesive strips or custom fitting of the strut to the exterior nasal surface contour may be selected as means for securing the long leg of the strut to the nose. The increased diameter and shortened length of the nasal passage increases air flow—including air flow necessary to sweep infused oxygen into the lungs—. At the same time, the device is highly effective in positioning the oxygen delivery stubs deep within the nostrils and providing substantial retention thereof. In addition , by eliminating ear loops that are causative of the abrasions, irritations and displacements discussed above, greater consistency in oxygen delivery is provided.

FIG. 6 illustrates a second preferred embodiment of the present invention obviating the need for ear loop technology. The retainer illustrated in FIG. 6, utilizes a curved portion 82 of short leg 74 in order to retain, stabilize and position oxygen barrel 76 under the nose and oxygen delivery stubs 79 within the nostrils 80. The retainer is comprised of a generally "L"-shaped strut 70 having a long leg 72 and a short leg 74. The strut is secured to the nose 88 by means of tape 86, adhesive materials, adhesive backings or, in some instances, by conforming the strut to the shape of the patient's nose so precisely as to remain in place without need of fixation means. The strut is extended superiorly to the root 85 of the nose. The short leg 74 of the strut 70 includes a curved portion 82 especially shaped, configured and adapted for receipt and retention of an oxygen delivery barrel 76. The oxygen delivery barrel 76 includes 2 oxygen delivery stubs 79 in fluid communication with the oxygen delivery barrel 76 and distal ends of the oxygen delivery tubes 94. However, it is equally contemplated that, in addition to the aforementioned short leg, a cup-shaped portion of the strut, generally at a similar angular relation with the long leg, may incorporate finger-like projections to retain, position and stabilize the oxygen delivery barrel and the oxygen delivery stubs arising therefrom.

An oxygen supply source provides pressurized oxygen to an oxygen supply tube 91 which, in turn, communicates at a distal end thereof with proximal ends of the delivery tubes 94. However, in the second preferred embodiment of the present invention, and, unlike the prior art, the oxygen delivery tubes arise at right angles 71 from the ends of the supply barrel 76 especially configured and conformed for right angle tube engagement. Also, instead of routing the delivery tubes behind the ears into "ear loops", the supply lines are routed upwards towards the midline of the long leg of the retainer strut 70 where the tubes are joined and affixed to the strut. In FIG. 6, the delivery tubes are held in close proximity to each other as well as the midline of the long leg 72 by means of tube retention pins 96. However, any suitable means such as, for example, adhesives, adhesive tape, cements, bonding agents, nylon ties and any other means capable of joining the supply lines to each other and the long leg may be utilized and are contemplated by the present invention. The delivery lines are joined together, above the long leg. This may be accomplished by molding the tubes to such a configuration, utilizing adhesives, nylon ties, or any other fixation means capable of holding the lines together. Thereafter, the delivery tubes are routed over the forehead and on to an oxygen supply tube.

By placing the retainer upon a patient's nose 98, and urging and securing the long leg of the strut against the ridge pole of the nose and upward towards the root 85, the resulting flexing of the strut, in restoring the original shape thereof and in opposition to means securing the long leg of the strut to the ridge pole region of a user's nose, tends to move the tip of the nose upward and inward, thereby shortening and widening the external nasal passages as compared to the undisturbed nasal bore. Adhesive backing, adhesive strips or custom fitting of the strut to the exterior nasal surface contour may be selected as means for securing the long leg of the strut to the nose. The increased diameter and shortened length of the nasal passage increases air flow—including air flow necessary to sweep infused oxygen into the lungs—. At the same time, the device is highly effective in positioning the oxygen delivery stubs deep within the nostrils and providing substantial retention thereof. In addition , by eliminating ear loops that are causative of the abrasions, irritations and displacements discussed above, greater consistency in oxygen delivery is provided. The second embodiment, incorporating right angle delivery tube connections with the oxygen supply barrel, further reduces lateral extension of tubing from the catheter/cannula. Therefore, lever arm force applied to the catheter/cannula that would otherwise tend to displace the device is further diminished.

FIG. 7 illustrates a third preferred embodiment of the present invention obviating the need for ear loop technology. The retainer illustrated in FIG. 7, utilizes a curved portion 112 of short leg 104 in order to retain, stabilize and position oxygen barrel 106 under the nose and oxygen delivery stubs 109 within the nostrils 110. The retainer is comprised of a generally "L"-shaped strut 100 having a long leg 102 and a short leg 104. The strut is secured to the nose 108 by means of tape 116, adhesive materials, adhesive backings or, in some instances, by conforming to the shape of the patient's nose so precisely as to remain in place without need of fixation means. The strut is extended superiorly to the root 115 of the nose. The short leg 104 of the strut 100 includes a curved portion 112 especially shaped, configured and adapted for receipt and retention of an oxygen delivery barrel 106. The oxygen delivery barrel 106 includes 2 oxygen delivery stubs 109 in fluid communication with the oxygen delivery barrel 106 and distal end of the oxygen delivery tube 124. However, it is equally contemplated that, in place of the afore-mentioned short leg, a cup-shaped portion of the strut, generally at a similar angular relation with the long leg; may incorporate finger-like projections to retain, position and stabilize the oxygen delivery barrel and the oxygen delivery stubs arising therefrom.

An oxygen supply source provides pressurized oxygen to an oxygen supply tube 121 which, in turn, communicates at a distal end thereof with proximal end of the delivery tube 124. However, in the third preferred embodiment of the present invention, and, unlike the prior art, a single oxygen delivery tube 124 arises from the middle of the supply barrel 106, between with the oxygen supply stubs 109. Also, instead of routing the delivery tubes behind the ears into "ear loops", the solitary supply line is routed upwards towards the midline of the long leg of the retainer strut 100 where the tube is affixed to the strut. In FIG. 7, the delivery tube is held in close proximity to the midline of the long leg 102 of the strut by means of tube retention pins 126. However, any suitable means such as, for example, adhesives, adhesive tape, cements, bonding agents, nylon ties and any other means capable of joining the supply lines to each other and the long leg may be utilized and are contemplated by the present invention. Superior to the long leg, the delivery line is routed over the forehead and on to an oxygen supply tube.

By placing the retainer upon a patient's nose 108, and urging the long leg of the strut against the ridge pole of the nose and upward towards the root 115, the resulting flexing of the strut, in restoring the original shape thereof, tends to move the tip of the nose upward and inward, thereby shortening and widening the external nasal passages as compared to the undisturbed nasal bore. The increased diameter and shortened length of the nasal passage increases air flow—including air flow necessary to sweep infused oxygen into the lungs—. At the same time, the device is highly effective in positioning the oxygen delivery stubs deep within the nostrils and providing substantial retention thereof. In addition, by eliminating ear loops that are causative of the abrasions, irritations and displacements discussed above, greater consistency in oxygen delivery is provided. The third embodiment, incorporating a single, centered (in regards to the length of the oxygen delivery barrel and midline of the nose) delivery tube connection, further reduces lateral extension of tubing from the catheter/cannula. Therefore, lever arm force applied to the catheter/cannula that would otherwise tend to displace the device is further diminished.

Each of the aforementioned embodiments of the present invention may advantageously include a straight edge surface 41, above and behind the patient's head, and parallel to the floor. This straight edge 41 is provided at a point behind and above the patient's head. By running the delivery lines—which, in the case of paired tubes, are joined together, distal to the retainer by the means described above—over the patient's forehead and thence up and over a suitable straight edge, free movement of the tubing greatly relieves tension on the catheter/cannula during head and body movements. More specifically, the oxygen delivery tube(s), affixed along the long leg of the strut and joined to an single oxygen supply tube at or proximal to the strut, is passed directly back and across the patient's forehead. The supply line then passes over the straight edge 41 parallel to the floor and slightly above the patient's head. The parallel edge allows smooth and rapid movement of the supply tube without causing any torsion or traction forces to be applied to the catheter/cannula during head movement. The straight edge utilized may be, for example, a hanger fitted to an IV stand 71 or hospital bed. In some instances, a headboard 41 may provide a suitable surface. Alternatively, the tubing could pass through an elevated round loop 111. In certain embodiments it may be advantageous to apply a minor amount of weight, just sufficient enough to prevent tangling of the tubing on the distal side of the hole or straight edge. In this way, patient movements would not allow for the formation of tangles. However, the tension must be kept sufficiently low so as to avoid any restriction of patient head movement.

In a first alternate method of the present invention, the catheter/cannula support device of the present invention can be utilized without a catheter/cannula or an oxygen source and still provide increased respiratory performance. In this embodiment, the shortening and increase in bore diameter of the external nasal passages increases breathing efficiency. This embodiment can be of great benefit to patients suffering from nasal congestion and or anatomic deformation which tend to obstruct the nasal passages. The increase in external nasal bore with a simultaneous decrease in passage length results in a significant decrease in resistance to gaseous exchange. Thus, the need for mouth breathing is reduced, respiration is facilitated and associated snoring may be eliminated. It is also believed that the reduction in breathing related stress may also reduce the risk of an untoward cardiac events.

The terms and expressions which have been employed in the foregoing specification are used therein as terms of description and not limitation, and there is no intention, in the use of such terms and expressions, of excluding equivalents of the features shown and described or portions thereof, it being recognized that the scope of the invention is defined and limited only by the following claims

I claim:

1. A nasal cannula support device comprising:
   a generally L-shaped strut having a long leg and a short leg;
   a means of securing said strut to a user's nose;
   a means of securing an oxygen supply barrel to said support device; and
   a tube management means wherein said long leg is securable to a ridge pole of a user's nose in such a manner as to raise and shorten the tip of the user's nose.

2. The nasal cannula support device of claim 1 wherein the short leg and the long leg of the strut junction in such an angular relationship so as to allow the short leg to pass around and under a user's nose tip when the long leg is positioned and secured in general alignment with a ridge pole of the user's nose and wherein when said strut is so secured, the tip of a user's nose is raised and shortened.

3. The nasal cannula support device of claim 1 wherein said means of securing the oxygen supply barrel is comprised of a portion of the strut especially shaped, configured and adapted for securing and positioning an oxygen delivery, barrel having a central bore and a pair of oxygen delivery stubs mounted transversely thereupon, so that said stubs align with the nostrils of a user.

4. The nasal cannula support device of claim 3 wherein said stubs also having central bores are in fluid communication with the central bore of said barrel and wherein said barrel is in fluid connection with at least one oxygen delivery tube.

5. The nasal cannula support device of claim 4 wherein said at least one oxygen delivery tube is in fluid communication with a source of pressurized oxygen.

6. The nasal cannula support device of claim 4 wherein said tube management means enables fixation of the at least one oxygen delivery tube to the long arm of said strut.

7. The nasal cannula support device of claim 6 wherein said tube management means is comprised a plurality of projections arising from said long leg wherein said projections are adapted about, so as to retain, the at least one oxygen delivery tube to the long arm of the strut.

8. The nasal cannula support device of claim 6 wherein the said tube management system is comprised of an adhesive compound of sufficient strength and material compatibility so as to enable fixation of the at least one oxygen delivery tube to the long arm of the strut.

9. The nasal cannula support device of claim 6 wherein the tube management system is comprised of adhesive tape of sufficient strength as to enable fixation of said at least one oxygen delivery tube to said long arm of the strut.

10. The nasal cannula support device of claim 6 wherein the tube management system is comprised of nylon ties so as to enable fixation of said at least one oxygen delivery tube to said long arm of the strut.

11. The nasal cannula support device of claim 6 wherein the tube management system is comprised of fabric having hook and loop fasteners with sufficient strength as to enable fixation of said at least one oxygen delivery tube to said long arm of the strut.

12. The nasal cannula support device of claim 3 further comprising a cup-shaped region located at, and extending laterally from, a juncture of the short and long leg of said L-shaped strut and wherein said cup-shaped portion is especially shaped, configured and adapted to engage the tip of a user's nose.

13. The nasal cannula support device of claim 1 wherein said device further includes a plurality of laterally spaced finger-like projections arising and extending from from said cup-shaped region, said finger-like projections being affixed to and further securing said barrel to said device.

14. The nasal cannula support device of claim 13 wherein said device includes, as an integral molded unit, said oxygen delivery barrel having said delivery stubs.

15. The nasal cannula support device of claim 14 wherein said device includes, as an integral and molded unit, said oxygen delivery barrel and said at least one oxygen delivery tube.

16. The nasal cannula support device of claim 1 wherein said strut is comprised of a material with sufficient elasticity so as to allow said long leg to be biased against, so as to conform with the user's external nasal surface contour.

17. The nasal cannula support device of claim 1 wherein said means of securing said device to a user's nose is an adhesive backing positioned and located on an undersurface of the strut.

18. The nasal cannula support device of claim 1 wherein said means of securing said device to a user's nose is provided by applying adhesive strips to both the strut and the user's skin lateral to the long leg of the strut.

19. The nasal cannula support device of claim 1 wherein said strut is especially shaped and formed so as to conform to an external surface contour of a user's nose and wherein said strut is comprised of a material having sufficient pliability and elastic memory as to allow said retainer to be retained upon said user's nose without any additional means of securing said strut to the user.

20. A nasal cannula apparatus comprising
a generally L-shaped strut having a long leg and a short leg;
an oxygen delivery barrel having two oxygen delivery stubs arising transversely therefrom;
a means of securing the strut to a user's nose; and
a tube management means wherein when said strut is secured to a user's nose along the ridge pole thereof the user's nose tip is both shortened and raised.

21. The nasal cannula apparatus of claim 20 wherein said oxygen delivery barrel is of an elongated cylindric configuration, said cylinder having a central bore which is in fluid communication with central bores of the two oxygen delivery stubs mounted transversely thereupon, and wherein said barrel is also in fluid communication with a central bore of at least one oxygen delivery tube connected thereto, said barrel being especially configured and adapted for placement under a user's nostrils in such a manner and position that said oxygen delivery stubs are positioned within said nostrils.

22. The nasal cannula apparatus of claim 21 wherein said short leg junctions with the long leg in such an angular relationship so that the short leg passes around and under a user's nose tip and wherein a portion of said strut is especially shaped, configured and adapted for securing, engaging and positioning said oxygen delivery barrel so that said delivery stubs are secured and positioned with the user's nostrils.

23. The nasal cannula apparatus of claim 22 wherein said oxygen delivery barrel is especially configured and adapted and is in fluid communication with two oxygen delivery tubes.

24. The nasal cannula apparatus of claim 23 wherein said two oxygen delivery tubes junction and connect with said barrel at opposite ends of said barrel and in axial alignment with the longitudinal axis thereof.

25. The nasal cannula apparatus device of claim 24 wherein said oxygen delivery tubes and barrel are integral and formed as one unit.

26. The nasal cannula apparatus of claim 23 wherein said two delivery tubes junction and connect with said oxygen delivery barrel at right angles to the longitudinal axis thereof.

27. The nasal cannula apparatus of claim 26 wherein said oxygen delivery tubes and barrel are integral and formed as one unit.

28. The nasal cannula apparatus of claim 22 wherein said oxygen delivery barrel is especially configured and adapted for fluid communication with one oxygen delivery tube.

29. The nasal cannula apparatus of claim 28 wherein said one oxygen delivery tube junctions and connects with said barrel at about the middle of the length of said barrel.

30. The nasal cannula apparatus of claim 29 wherein said oxygen delivery tube and barrel are formed as one integral unit.

31. The nasal cannula apparatus of claim 22 wherein said strut includes a cup-shaped region at, and extending laterally from, the juncture of the short and long leg of said L-shaped strut and wherein said cup-shaped portion is especially shaped, configured and adapted to engage the tip of a user's nose.

32. The nasal cannula apparatus of claim 31 wherein said device further includes a plurality of laterally spaced finger-like projections arising and extending from from said cup-shaped region, said finger-like projections entering into and further securing said barrel to said device.

33. The nasal cannula apparatus of claim 21 wherein said at least one oxygen delivery tube is in fluid communication with an oxygen supply tube.

34. The nasal cannula apparatus of claim 31 wherein said at least one oxygen delivery tube is in fluid communication with a source of pressurized oxygen.

35. The nasal cannula apparatus of claim 34 wherein an oxygen supply tube provides a conduit from the source of pressurized oxygen to the at least one oxygen delivery tube.

36. The nasal cannula apparatus of claim 35 further comprising a straight edge surface positioned above and behind a user's head and wherein said straight edge is parallel to a floor supporting the user and wherein said oxygen supply tube can pass through said loop so as to provide free movement thereto and so as to reduce tension and displacement forces otherwise transmitted to the cannula during user head movements.

37. The nasal cannula apparatus of claim 36 wherein said straight edge is a head board.

38. The nasal cannula apparatus of claim 36 wherein said straight edge is mounted upon a portable stand.

39. The nasal cannula apparatus of claim 35 further comprising a loop located behind and above the user and wherein said oxygen supply tube can pass through said loop so as to reduce tension and displacement forces otherwise transmitted to the cannula during user head movements.

40. The nasal cannula apparatus of claim 20 wherein said tube management means comprises adhesive tape applied to and affixing said at least one delivery tube to the long leg of the L-shaped strut.

41. The nasal cannula apparatus of claim 20 wherein said tube management means comprises fabric having hook and loop fasteners for securing said at least one oxygen delivery tube to the long leg of said L-shaped strut.

42. The nasal cannula apparatus of claim 20 wherein said tube management means comprises plastic lock ties utilized to secure said at least one oxygen delivery tube to the long leg of said L-shaped strut.

43. The nasal cannula apparatus of claim 20 wherein said delivery tube management means comprises a plurality of pliable prongs located upon and affixed to said long leg of said strut, said pliable prongs being especially configured and adapted so as to be easily bent about to secure said at least one oxygen delivery tube to the long leg of said strut.

44. The nasal cannula apparatus of claim 20 wherein the said strut is comprised of a material with sufficient elasticity so as to allow said long leg thereof to be conformed to the external surface contour of a user's nose.

45. The nasal cannula apparatus of claim 20 wherein said means of securing said apparatus to a user's nose is adhesive tape.

46. The nasal cannula apparatus of claim 20 wherein said means of securing said apparatus to a user's nose is an adhesive applied to an undersurface of the L-shaped strut.

47. The nasal cannula apparatus of claim 20 wherein said strut is especially shaped, configured and adapted so as to conform to a user's external nasal surface contour.

48. The nasal cannula apparatus of claim 47 wherein said strut is comprised of a material having sufficient pliability and elastic memory as to allow said conformance to the external surface contour of a user's nose to provide said means of securing said device to said user.

49. The nasal cannula apparatus of claim 20 wherein said tube management means comprises fabric having hook and loop fasteners wherein said fabric is utilized for securing said at least one oxygen delivery tube to the long leg of said L-shaped strut.

50. The nasal cannula apparatus of claim 20 wherein said tube management means comprises plastic lock ties wherein said lock ties are utilized to secure said at least one oxygen delivery tube to the long leg of said L-shaped strut.

\* \* \* \* \*